(12) United States Patent
Norton et al.

(10) Patent No.: US 6,753,961 B1
(45) Date of Patent: Jun. 22, 2004

(54) SPECTROSCOPIC ELLIPSOMETER WITHOUT ROTATING COMPONENTS

(75) Inventors: Adam E. Norton, Palo Alto, CA (US); Kenneth C. Johnson, Santa Clara, CA (US); Fred E. Stanke, Cupertino, CA (US); Abdurrahman Sezginer, Los Gatos, CA (US)

(73) Assignee: Therma-Wave, Inc., Fremont, CA (US)

( * ) Notice: Subject to any disclaimer, the term of this patent is extended or adjusted under 35 U.S.C. 154(b) by 317 days.

(21) Appl. No.: 09/956,356

(22) Filed: Sep. 18, 2001

Related U.S. Application Data
(60) Provisional application No. 60/233,163, filed on Sep. 18, 2000.

(51) Int. Cl.[7] .................................................. G01J 4/00
(52) U.S. Cl. ...................................................... 356/364
(58) Field of Search ............................... 356/364, 365, 356/368, 369; 355/53

(56) References Cited

U.S. PATENT DOCUMENTS

| | | | | |
|---|---|---|---|---|
| 5,018,863 A | * | 5/1991 | Vareille et al. | 356/369 |
| 5,872,630 A | * | 2/1999 | Johs et al. | 356/369 |
| 6,052,188 A | * | 4/2000 | Fluckiger et al. | 356/369 |
| 6,134,012 A | * | 10/2000 | Aspnes et al. | 356/369 |
| 6,256,097 B1 | * | 7/2001 | Wagner | 356/369 |
| 6,307,627 B1 | * | 10/2001 | Vurens | 356/369 |

OTHER PUBLICATIONS

K. Oka et al., "Spectroscopic polarimetry with a channeled spectrum," *Optics Letters*, vol. 24, No. 21, Nov. 1, 1999, pp. 1475–1477.

* cited by examiner

*Primary Examiner*—David Gray
*Assistant Examiner*—D. Ben Esplin
(74) *Attorney, Agent, or Firm*—Stallman & Pollock LLP

(57) ABSTRACT

A spectroscopic ellipsometer having a multiwavelength light source, spectrometer (or wavelength-scanning monochromator and photodetector), a polarizer and polarization analyzer, and one or more objectives in the illumination and collection light paths, further comprises a stationary polarization modulator that modulates the light polarization versus wavelength. Modulator can be an optically active crystal rotating the linear polarization plane by a different angle for each wavelength or a non-achromatic waveplate retarder that varies the relative phase delay of the polarization components periodically over wavelength. The measured spectrum can be used to characterize selected features or parameters of a sample, e.g. by comparison with one or more theoretical spectra.

29 Claims, 2 Drawing Sheets

SPECTROSCOPIC ELLIPSOMETER WITHOUT ROTATING COMPONENTS

CROSS-REFERENCE TO RELATED APPLICATION

This application claims priority under 35 U.S.C. 119(e) from prior U.S. provisional application No. 60/233,163, filed Sep. 18, 2000.

TECHNICAL FIELD

The present invention relates to ellipsometers and in particular to small-spot spectroscopic ellipsometers.

BACKGROUND ART

In a conventional ellipsometer, the polarization is modulated by a rotating element—either a polarizer or quarter wave plate—placed either before or after the sample. On the other side lies a polarizer or waveplate polarizer combination. By measuring the signal at several different positions of the rotating component (a minimum of four), the ellipsometric parameters psi ($\Psi$) and delta ($\Delta$), or more usually tan $\Psi$ and cos $\Delta$, are determined. The ellipsometer may function at one wavelength or many wavelengths, in which case it is called a spectroscopic ellipsometer.

With a single wavelength only two parameters are measured and therefore only two unknowns can be determined, for example, thickness and index of a single layer film. With a spectroscopic ellipsometer, there are two independent parameters measured at each wavelength and many more sample unknowns can be determined. Typically, though, the unknowns are not completely independent with wavelength. Film thickness is constant versus wavelength, and refractive index obeys dispersion relationships that can be approximated by many different formulae. These formulae may have only a few independent coefficients to specify the index for several hundred or thousand wavelength data points.

A regression procedure is usually performed where the unknowns are varied to produce theoretical spectra of tan $\Psi$ and cos $\Delta$, or $\Psi$ and $\Delta$, or another set of ellipsometric parameters, alpha ($\alpha$) and beta ($\beta$), that best matches the ones measured from the sample. Depending on the quality of the data and the correlation of the unknowns, the maximum number of unknowns that may be regressed is usually less than 8 or 10 even though there are usually between 265 and 2048 separate spectral data points. Many of these points are clearly redundant, a fact that is exploited by the present invention.

One of the biggest problems in constructing any ellipsometer is the rotating mechanical components which must be very precise and: are relatively large since the light goes through the center shaft. Both the size and complexity are big disadvantages for integrated ellipsometers which must be compact and relatively inexpensive. An integrated instrument is one that is located within or attached to a process tool, such as a semiconductor wafer resist development track, that is helping to produce the samples which are to be measured.

Another problem for small spot spectroscopic ellipsometers is the limited light that is available. When a laser can not be used for the light source, there are fundamental limits to the brightness with which a small spot on the sample can be illuminated. Usually the signal for a small spot spectroscopic ellipsometer must integrated over some fraction of the period of the rotating element, and then a few turns are averaged together.

There have been other designs for ellipsometers with no moving parts, but none that have been ideal for a small-spot, integrated, spectroscopic ellipsometer. One design uses an acousto-optic modulator in place of the rotating element, but these vibrate at a high frequency meaning that it is impossible to integrate the signal for very long. These also do not work well over a very broad spectral range.

Another design directs light from different portions of the beam aperture to different analyzers and detectors where the analyzers are mounted at different fixed angles. For a spectroscopic ellipsometer, this design would either require multiple spectrometers and be very expensive, or a monochromator in the illumination and be very slow. The light level on each detector would also be reduced. In a small spot ellipsometer, breaking the aperture into separate beams also increases the diffraction limited spot size on the water.

Another design uses arrangements of polarizing beamsplitters and waveplates to send differently polarized beams to different detectors. Again, this scheme would require multiple spectrometers or a monochromator if it is to be spectroscopic. The wavelength range is also limited due to the imperfectly achromatic waveplates.

An object of this invention is to provide a small-spot, spectroscopic ellipsometer with no rotating elements that is suitable for an integrated instrument. The wavelength range can encompass the UV through near IR. The VUV and far IR ranges may be measured with a different choice of components.

DISCLOSURE OF THE INVENTION

The basic concept of the invention is that the polarization is modulated with respect to wavelength instead of time as in a conventional ellipsometer.

The spectroscopic ellipsometry instrument includes (1) a multiwavelength light source providing a light, beam in an illumination optical path directed toward a sample surface under examination, (2) a spectrometer receiving light through an aperture in a collection optical path from the sample surface and providing a spectroscopic measurement signal to an ellipsometry data processor, (3) optionally, at least one objective in the illumination and collection paths focusing the light beam and gathering light from a small spot (e.g. a size less than 500 $\mu$m) on the sample surface, (4) a polarizer and polarization analyzer of known orientation in the illumination and collection paths, and (5) a stationary polarization modulator in at least one of the illumination and collection optical paths, wherein the modulator modulates the light polarization cyclically (e.g., pseudo-periodically or sinusoidally) versus wavelength, the polarization being modulated by at least one-half period over a wavelength range of the instrument. Several ellipsometer embodiments are described in further detail below, differing in using oblique or perpendicular incidence on the sample, using completely separate illumination and collection light paths with two objectives and separate polarizer and polarization analyzing elements or using a beamsplitter with a portion of the illumination and collection paths between the beamsplitter and sample being in common and with a single common objective, and also differing in the placement of the modulator. This polarization-versus-wavelength modulation concept may be applied to large-spot spectroscopic ellipsometers as well.

Figure 1:
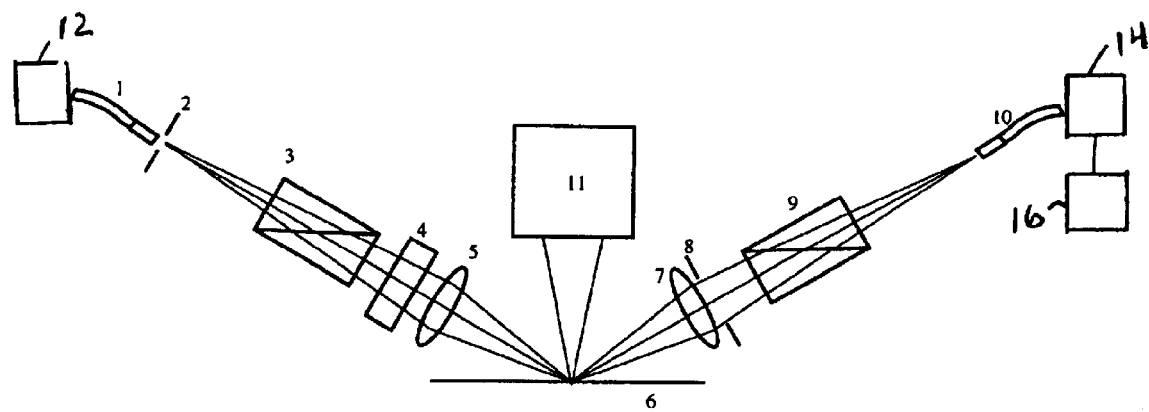
FIG. 1 is a side schematic view of a first embodiment of a spectroscopic ellipsometer of the subject invention having non-normal illumination and collection paths.

The light source 12 (which can include a monochrometer) is connected to the far end of the illumination fiber 1 or 20, and the spectrometer (or detector) 14 is connected to the far end of the optical fiber 10 or 29 and are conventional. An ellipsometry data processor 16 receives ellipsometry data from the spectrometer. These elements are described below.

Reference Numerals

1. Illumination fiber
2. Slit
3. Polarizer
4. Polarization modulator
5. Illumination objective
6. Sample
7. Collection objective
8. Aperture
9. Polarization analyzer
10. Spectrometer fiber bundle
11. Viewing optics
12. Light source (monochrometer)
14. Spectrometer/detector
16. Data processor
20. Illumination fiber
21. Condenser lens
22. Field stop
23. Beamsplitter
24. Polarizer
25. Polarization modulator
26. Objective
27. Sample
28. Reflective pinhole
29. Spectrometer fiber
30. Viewing optics
31. Aperture

BEST MODE OF CARRYING OUT THE INVENTION

FIG. 1 is a diagram of the best embodiment of the invention for a reflective sample. It can also be used in transmission mode if one of the arms is on the opposite side of the sample.

The illumination fiber 1 carries light from preferably a xenon lamp illuminator to the optional slit 2. The fiber 1 is preferably a single multimode silica core silica clad fiber. While the fiber 1 is helpful for packaging an integrated system, the illumination may also be focused directly in a more conventional manner onto the slit 2. The slit 2 helps restrict the size of the illuminated area on the sample 6. The polarizer 3 lets pass only linearly polarized light. Since it does not rotate it may be any number of crystal polarizer designs that may or may not deviate the light. Dichroic or thin film polarizers are not well-suited since their extinction ratios are low. The polarizer may also be combined with a waveplate to produce elliptical polarization.

The modulator 4 may be of two different types. The first is a piece of crystal quartz with the optical axis parallel to the optical path. When used in this orientation, the quartz is an optically active crystal that rotates the plane of the linearly polarized light to a different angle for each separate wavelength. One disadvantage with this type is that the change in angle versus wavelength is much greater in the UV and blue than it is for the red and IR. A thick optically active crystal will create a difference in polarization orientation between different parts of the spectrum of more than 360 degrees causing the rotation to vary cyclically versus wavelength. The second type, which is preferred, uses a piece of quartz or other birefringent crystal with its optical axis perpendicular to the light path and preferably at 45 deg. to the polarization plane of the polarizer 3. In this case the modulator 4 is a non-achromatic waveplate where the phase delay varies cyclically versus wavelength, but not exactly sinusoidally versus wavelength. As the wavelength varies, the polarization state after the modulator changes from linear, to circular, to the perpendicular linear, to reverse circular, and back to the original linear. To sample the variation adequately, there should be at least four pixels in the spectrometer per every period of polarization modulation. The modulator may also be placed in the collection path before the analyzer. There may even be modulators in both arms with differing, wavelength-dependant characteristics.

The illumination objective 5 focuses an image of the fiber end and slit 2 onto the sample 6. The objective may also be a concave mirror or reflective lens system. The collection objective then gathers the reflected light to form an image of the sample on the spectrometer fiber 10. The two objectives can be designed to compensate for the spherical and chromatic aberration introduced by the polarizer and modulator. Alternatively, the light may be collimated as it passes through the polarizer, modulator, and analyzer by putting a lens between the slit 2 and the polarizer 3 and also between the analyzer 9 and the spectrometer fiber 10. Collimating the light through the modulator will eliminate an axially offset double image in the version that relies on non-achromatic retardance. The aperture 8 blocks unwanted light that may scatter from adjacent patterns on the wafer. The analyzer 9 is another polarizing crystal prism that serves a similar function as in other ellipsometers, that is, to select a polarization. The analyzer may also have a waveplate in front of it. The spectrometer fiber bundle 10 sends the light to a spectrometer. Typically, the spectrometer signal is then digitized and sent to a computer for processing. The fiber bundle face should be slightly smaller then the size of the spot projected on to it so that the signal is not overly sensitive to sample focus. Optionally, there may be a slit in front of the bundle to match the shape of the slit in the illuminator. If there is space in the instrument to place the spectrometer entrance slit at this point, then the fiber bundle 10 is not needed. The viewing optics 11 allow the system or operator to move the pattern requiring measurement. This subsystem can also incorporate an autofocus system.

The light path before the sample is called the illumination path, and the light path after reflection or transmission from the sample is called the collection path.

Aside from the mechanical simplicity of this system, another advantage is that the stationary optics allow the signal to be integrated for as long as is necessary. Integration is much more effective at removing noise than is averaging multiple spectra.

To determine the unknown characteristics of the sample, the algorithms should ideally know parameters of the system such as the polarizer orientation, modulator orientation and its wavelength-dependent retardance, analyzer orientation, system transmission/detector response versus wavelength, angle of incidence, and numerical aperture. The algorithm "floats" sample unknowns to determine their values. Initial estimates of the sample unknowns are used together with the known sample and system parameters to calculate one or more initial theoretical intensity spectra based on a theoretical model that simulates the interaction of light with the sample. A data base of many spectra may also be generated from the model for ranges of values of the sample unknowns so that the calculation does not need to be done in real time. An optimization procedure is then performed to choose and/or modify the unknown parameters to achieve the best fit between the theoretical and measured intensity spectra. In practice, some of the system parameters such as angle of incidence may also be floated as unknowns. Floating a multiplicative factor for system transmission can correct for long term drift in the light source. Long term drift can also be corrected by having the system measure a sample of known reflectance sitting next to the unknown sample.

In order to know the critical parameters of the system optics, they must either be determined through calibration, measured off line, or adjusted carefully to known values. Calibration of all significant unknown system optical parameters may require one or more different samples with known film thickness and refractive index. The system optical parameters may then be regressed until the theoretical spectra match the measured spectra on the calibration samples. However, the number of calibration samples may be reduced if some of the optical parameters are measured off-line or are carefully adjusted. For example, the retardance of the waveplate versus wavelength may be measured before it is installed in the system. The polarizer and modulator could then be aligned using, for example, the following procedure: remove the analyzer, load a bare silicon sample, adjust both the polarizer and modulator to minimize the minima in the spectrum. In this condition, the polarizer axis would be in either the S or P planes, and the modulator axis would be at 45° to the plane of incidence. The best orientation of the analyzer axis would then be close to 45° to the plane of incidence. While the orientations described above will likely give good results, the optimal orientations may depend on the sample type and may need to be determined through simulation.

When measuring the polarizing characteristics of a grating-like structure to determine the profile of the grating, it may be advantageous to use an ellipsometer with a normal, i.e. perpendicular (0°) angle of incidence. In this case, another embodiment of the invention may be made as shown in FIG. 2.

Figure 2:
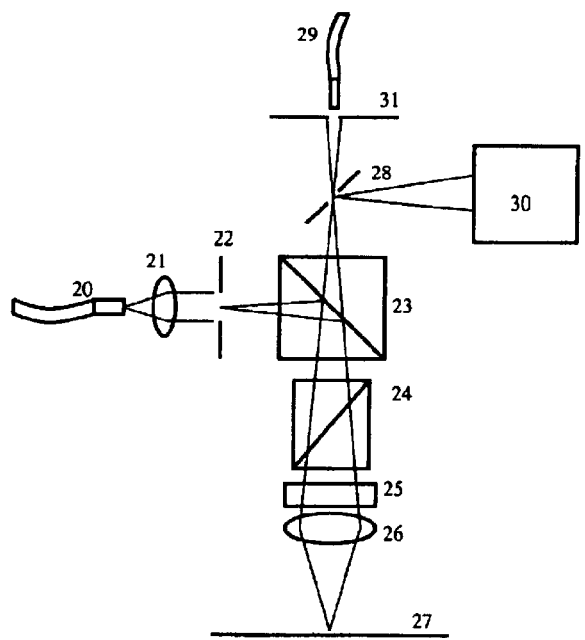
FIG. 2 is a side schematic view of a second embodiment of a spectroscopic ellipsometer of the subject invention having a normal illumination angle of incidence and where a polarization modulator is located in both the illumination and collection paths.

In FIG. 2, the output end of illumination fiber 20 and condenser lens 21 provide Kohler illumination for the entire field of view on the sample 27. The field stop 22 is conjugate to the sample and defines the boundaries of the field illumination. The beamsplitter 23 directs part of the light to the polarizer 24 which serves a function similar to both the polarizer and analyzer in FIG. 1. The modulator 25 serves a similar purpose to the modulator in FIG. 1 except that the light passes through it twice. The objective 26 both focuses the illumination on to the sample 27 and collects the light reflected from the sample imaging it on to the reflective pinhole 28. The reflected light then passes through the modulator 25 again. It then passes through the polarizer 24 again which now serves the same function as the analyzer in FIG. 1. The pinhole 28 then allows light from only a small area on the sample to pass to the spectrometer fiber. The aperture 31 effectively reduces the numerical aperture on the wafer of the light used for measurements without affecting the resolution of the viewing optics. The remaining light that reflects from the pinhole goes to the viewing optics to allow the sample pattern to be viewed and possibly focused. If the instrument has a separate viewing system with a known distance separating them, then the viewing optics 30 are not necessary. This could be implemented as a separate system that moves together with the ellipsometer optics.

The beamsplitter 23 and polarizer 24 could also be combined into a polarizing beamsplitter; either a thin film polarizer or one based on a glan-thompson design.

As with the embodiment in FIG. 1, it may be optically advantageous to have collimated light passing through the beamsplitter, polarizer and modulator. This can be done with a lens between the field stop 22 and the beamsplitter 23, and also one between the beamsplitter 23 and the pinhole 28.

One unique feature of the embodiment in FIG. 2 is that light is normally incident to the sample, within the restrictions of the system's numerical aperture. Other ellipsometers used to measure polarizing properties of grating-like reflective samples have only used near-normally-incident light due to the limitations of conventional ellipsometer design. Having the light incident substantially normal to the sample means that it may not be necessary to rotationally orient the sample relative to the ellipsometer optics or vice versa.

Also, if the modulator 25 is temporarily removed from the beam path, the instrument can function like a conventional small-spot reflectometer. Such a configuration is unique in that it has an optical head moving as a single unit with illumination fed to it via a fiber optic and collected light fed into a fiber leading to a spectrometer. The spectrometer may be mounted to the moving optical head, or it may be a stationary remote spectrometer, that is one that does not move with the optical head.

Figure 3:
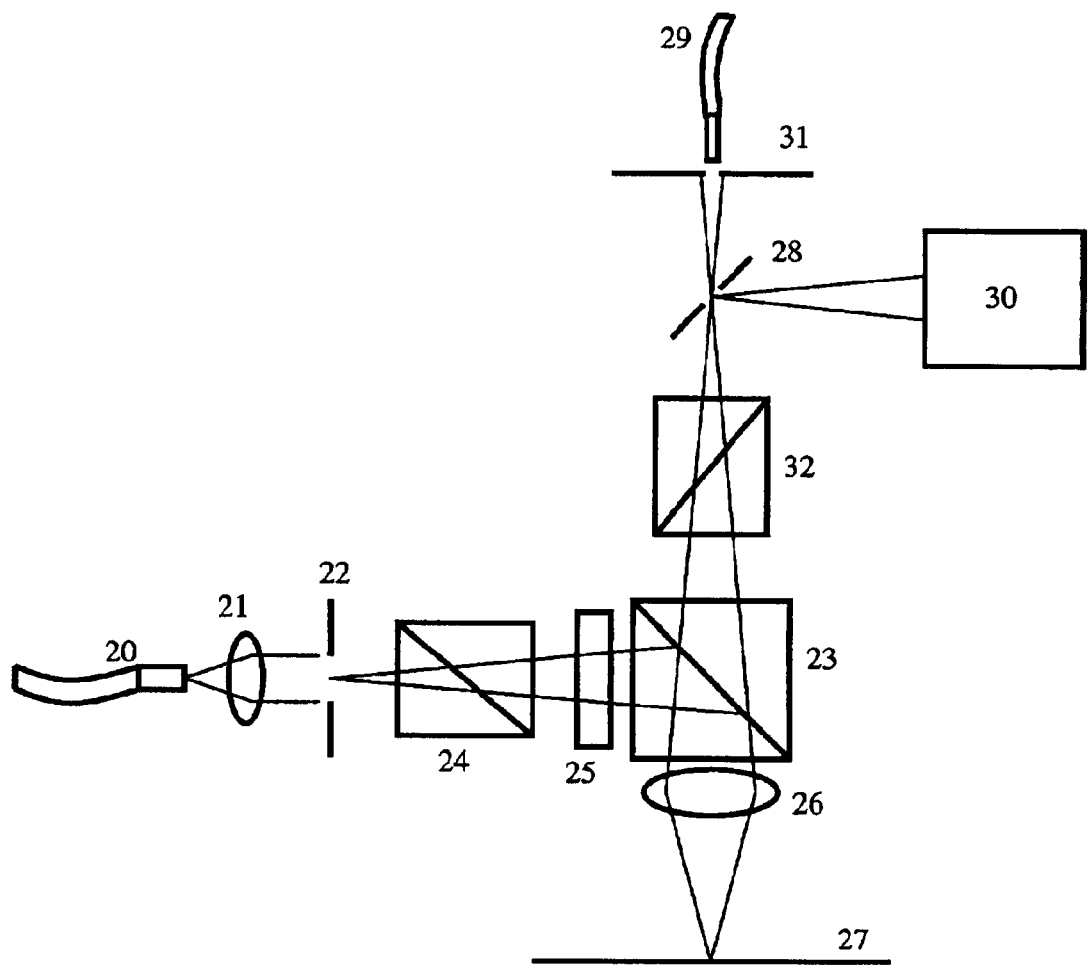
FIG. 3 is a side schematic view of a third embodiment of a spectroscopic ellipsometer of the subject invention having a normal illumination angle of incidence and where a polarization modulator is located only in the illumination path.

A slightly different embodiment of the normal incident version is shown in FIG. 3. In this version the polarizer 24 and modulator 25 are placed in the illumination light before the beamsplitter 23. There is then an additional analyzer 32 that is placed between the beamsplitter 23 and the reflective pinhole 28. Equivalently, the modulator 25 may be placed instead between the beamsplitter 23 and the analyzer 32.

An advantage of the embodiment in FIG. 3 is that the light travels through the modulator only once which may allow for increased sensitivity to sample parameters. The disadvantage is that the optical characteristics of the beam splitter must also be calibrated. The characteristics of the polarizer, modulator and the reflective characteristics of the beamsplitter can thought of as one combined wavelength-dependent Jones matrix and calibrated as one unit. The same can be said for the analyzer and the transmission characteristics of the beamsplitter.

In all of the above embodiments, the spectrometer could be replaced by a simple photodetector and a scanning monochromator used in the light source instead. A tunable laser could also be used. The signal at each wavelength would then be measured in sequence as the monochromator scans.

As we described earlier, the modulators in above embodiments modulate the polarization with a period that is longer in wavelength than the resolution of the spectrometer. Since the optical properties of the sample also vary significantly over similar wavelength ranges, the above embodiments do not produce a measurement of the conventional ellipsometric parameters tan $\Psi$ and cos $\Delta$. In order to measure these, the modulator preferably has a period that is very short compared to the variation of the sample optical properties. One embodiment would then use a high-resolution spectrometer or monochromator to distinguish the different polarization states. However, these would be very large and expensive and impractical for an integrated instrument. Alternatively a low resolution spectrometer could be used together with an etalon. Etalons consist of parallel reflectors. Etalons have transmission spectra consisting of narrow peaks that repeat periodically. An etalon that has a period approximately matching the period of the modulator (at least over the resolution width of the spectrometer) will only allow only wavelengths corresponding to a particular polarization state to be transmitted to any given spectrometer pixel. By changing the separation of the etalon plates, a different polarization state is transmitted. In this manner, several spectra can be taken with different etalon spacings so that multiple polarization states are measured for each pixel. From these measurements, values for $\tan \Psi$ and $\cos \Delta$ can be calculated.

What is claimed is:

1. A spectroscopic ellipsometer, comprising:
   a multiwavelength light source providing a light beam in an illumination optical path directed toward a sample surface under examination;
   a spectrometer receiving light in a collection optical path from said sample surface and generating a spectroscopic measurement signal;
   a polarizer and polarization analyzer in the illumination and collection paths;
   a stationary polarization modulator in at least one of the illumination and collection optical paths, wherein said modulator modulates polarization versus wavelength, the polarization being modulated by more than one period over a wavelength range of the instrument; and
   a data processor for receiving the spectroscopic measurement signal, said processor generating a theoretical intensity spectrum based on a theoretical model that simulates the interaction of light with the sample using initial estimates of sample unknowns and uses an optimization procedure to modify the unknown parameters to achieve a best fit between the generated theoretical spectrum and the spectroscopic measurement signal.

2. The ellipsometer of claim 1 wherein the modulator is an optically active crystal, said crystal rotating the linear polarization plane of the light cyclically versus wavelength.

3. The ellipsometer of claim 1 wherein the modulator is a non-achromatic waveplate retarder such that the phase delay of the light varies cyclically versus wavelength.

4. The ellipsometer of claim 1 wherein the modulator is located in the illumination path of the light beam.

5. The ellipsometer of claim 1 wherein the modulator is located in the collection path of the light from the sample, the modulator being positioned in the collection path before the polarization analyzer.

6. The ellipsometer of claim 1 wherein the modulator is located in a common portion of both the illumination and collection paths.

7. The ellipsometer of claim 1 wherein the spectrometer receives light from a spot on the sample having a size smaller than 500 $\mu$m.

8. The ellipsometer of claim 1 wherein the light beam in the illumination path is incident on the sample surface at an oblique angle.

9. The ellipsometer of claim 8 wherein the illumination and collection paths are entirely separate, the ellipsometer having two objectives including an illumination objective in the illumination path for focusing the light beam to a spot on the sample and also a collection objective in the collection path for collecting light reflected from the spot on the sample, the polarizer and polarization analyzer comprising two distinct elements in the respective illumination and collection paths.

10. The ellipsometer of claim 1 further comprising a beamsplitter, a portion of the illumination and collection paths being in common between the beamsplitter and the sample, but the portion of the illumination path between the light source and the beamsplitter being separate from the portion of the collection path between the beamsplitter and the spectrometer, the ellipsometer having an objective in the common portion of the illumination and collection paths for focusing the light beam to a spot and collecting light reflected from that spot.

11. The ellipsometer of claim 10 wherein the light beam has substantially perpendicular incidence on the sample surface.

12. The ellipsometer of claim 10 wherein the modulator is located between the beamsplitter and the sample in the common portion of the illumination and collection paths.

13. The ellipsometer of claim 10 wherein the modulator is located in the separate portion of the illumination path between the light source and the beamsplitter, and also after the polarizer.

14. The ellipsometer of claim 10 wherein the modulator is located in the separate portion of the collection path between the beamsplitter and the spectrometer, and also prior to the polarization analyzer.

15. The ellipsometer of claim 10 wherein the polarizer and polarization analyzer are two distinct elements located in the respective separate portions of the illumination and collection paths.

16. The ellipsometer of claim 12 wherein the polarizer and polarization analyzer comprises a single polarizing element located in the common portion of the illumination and collection paths between the beamsplitter and the modulator.

17. The ellipsometer of claim 10 wherein the beamsplitter is a polarizing beamsplitter.

18. spectroscopic ellipsometer, comprising:
    a multiwavelength light source;
    a wavelength-scanning monochromator providing a light beam in an illumination optical path directed toward a sample surface under examination;
    polarizer and polarization analyzer in the illumination and collection paths;
    a stationary polarization modulator in at least one of the illumination and collection optical paths, wherein said modulator modulates polarization versus wavelength, the polarization being modulated by more than one period over a wavelength range of the instrument;
    a detector receiving light in a collection optical path from said sample surface and sequentially generating a spectroscopic measurement signal; and
    an ellipsometry data processor for receiving the spectroscopic measurement signal, said processor generating a theoretical intensity spectrum based on a theoretical model that simulates the interaction of light with the sample using initial estimates of sample unknowns and uses an optimization procedure to modify the unknown parameters to achieve a best fit between the generated theoretical spectrum and the spectroscopic measurement signal.

19. A spectroscopic ellipsometry method for measuring selected characteristics of a sample under examination, the selected sample characteristics affecting the sample's optical characteristics, including ellipsometric parameters, for multiple wavelengths, comprising:

directing multiwavelength polarized light at a spot on the sample, the polarized light interacting with the sample;

gathering light from the sample spot and measuring a value proportional to light intensity at multiple wavelengths to generate a measured spectrum, the spectral measurement being for gathered light of at least one selected polarization state;

modulating the polarization state of the light versus wavelength, the polarization modulation occurring anywhere in the path of the directed polarized light or the gathered light prior to the selection of the at least one polarization state for spectral measurement, wherein the polarization state of the light is varied using a stationary modulator which varies the polarization cyclically with wavelength and the spectrum is measured over a wavelength range of more than one cycle of the polarization-versus-wavelength modulation; and processing the measured spectrum to obtain a corresponding measure of the selected characteristics of the sample, said processing including generating a theoretical intensity spectrum based on a theoretical model that simulates the interaction of light with the sample using initial estimates of sample unknowns and uses an optimization procedure to modify the unknown parameters to achieve a best fit between the generated theoretical spectrum and the spectroscopic measurement signal.

20. The method of claim 19 wherein the spectrum is measured with a particular wavelength resolution and the polarization state of the light is modulated with a period smaller in wavelength than said resolution.

21. The method of claim 19 wherein the processing further includes a calibration using multiple samples of known film thickness and refractive index.

22. The method of claim 19 wherein the polarization modulating is carried out by an optically active crystal, said crystal rotating the linear polarization plane of the light cyclically versus wavelength.

23. The ellipsometer of claim 19 wherein the modulator is a non-achromatic waveplate retarder causing the phase delay of the light to vary cyclically versus wavelength.

24. The method of claim 19 wherein the spot on the sample has a size smaller than 500 $\mu$m.

25. The method of claim 19 wherein the light is directed at an oblique angle onto the example.

26. The method of claim 19 wherein the light is directed at a substantially perpendicular angle onto the sample.

27. The method of claim 19 further comprising measuring and processing said spectrum at a plurality of sample positions.

28. The method of claim 19 wherein a monochromator scans the directed light over wavelength and the spectrum is measured one wavelength at a time.

29. A spectroscopic ellipsometer of claim 1 further including an adjustable etalon located in one of the illumination and collection paths and wherein multiple measurements are taken at different etalon spacings.

* * * * *